United States Patent [19]

Stevens et al.

[11] Patent Number: 5,565,495

[45] Date of Patent: Oct. 15, 1996

[54] METHOD FOR SURVIVAL CURVE SHIFTING IN DOGS

[75] Inventors: David R. Stevens, Leawood; William W. Ruehl, Lake Quivera, both of Kans.

[73] Assignee: Deprenyl Animal Health, Inc., Overland Park, Kans.

[21] Appl. No.: 300,962

[22] Filed: Sep. 6, 1994

Related U.S. Application Data

[63] Continuation-in-part of Ser. No. 113,608, Aug. 27, 1993, Pat. No. 5,387,615, which is a continuation of Ser. No. 975,284, Nov. 12, 1992, Pat. No. 5,276,057, which is a continuation-in-part of Ser. No. 643,452, Nov. 8, 1991, abandoned, which is a continuation-in-part of Ser. No. 576,011, Aug. 3, 1990, Pat. No. 5,151,449.

[51] Int. Cl.$^6$ ................................................. A61K 31/135
[52] U.S. Cl. ........................................................... 514/646
[58] Field of Search ............................................. 514/646

[56] References Cited

U.S. PATENT DOCUMENTS

| | | | |
|---|---|---|---|
| 4,564,706 | 1/1986 | Escery et al. | 564/376 |
| 4,861,800 | 8/1989 | Buyske | 514/646 |
| 4,871,550 | 10/1989 | Millman | 424/601 |
| 4,880,833 | 11/1989 | Knoll et al. | 514/565 |
| 4,916,151 | 4/1990 | Berg et al. | 514/419 |
| 5,192,808 | 3/1993 | Ruehl et al. | 514/654 |
| 5,276,057 | 1/1994 | Milgram | 514/654 |

FOREIGN PATENT DOCUMENTS

| | | |
|---|---|---|
| 871155 | 5/1971 | Canada. |
| 1215394 | 12/1986 | Canada. |

OTHER PUBLICATIONS

Milgram, et al., "Maintenance on L–Deprenyl Prolongs Life in Aged Male Rats", Life Sciences, vol. 47, pp. 415–420. (1990).

Knoll, "Extension of Life Span of Rats by Long–Term (–)Deprenyl Treatment", The Mount Sinai Journal Of Medicine, vol. 55, No. 1, Jan. 1988, pp. 67–74.

Knoll, "The Striatal Dopamine Dependency of Life Span in Male Rats, Longevity Study with (–)Deprenyl", Mechanisms Of Aging And Developments, 46 (1988), 237–262.

Knoll, "The Pharmacology of Selective Mao Inhibitors", Monoamine Oxidase Inhibitors— The State Of The Art, 1981, pp. 45–61.

Knoll, et al., "Long–Lasting, True Aphrodisiac Efffect of (–)Deprenyl in Sexually Sluggish Old Male Rats", Modl Probl. Pharmacopsychiat., vol. 19, pp. 135, 153 (1983).

Kitani, et al., "Chronic Treatment of (–)Deprenyl Prolongs the Life Span of Male Fischer 344 Rats. Further Evidence", Life Sciences, vol. 52, 1993, pp. 281–288.

Knoll, et al., "Striatal Dopamine, Sexual Activity and Lifespan. Longevity of Rats Treated with (–)Deprenyl", Life Sciences, vol. 45, 1989, pp. 527–531.

Milgram, et al., "Maintenance on L–Deprenyl Prolongs Life in Aged Male Rats", Life Sciences, vol. 47, 1990, pp. 416–420.

*Primary Examiner*—Theodore J. Criares
*Attorney, Agent, or Firm*—Zarley, McKee, Thomte, Voorhees, & Sease

[57] ABSTRACT

Selegiline, or a pharmaceutically acceptable salt form of selegiline, is administered to mammals commencing at a point in time at which at least 50% of the mammal's life span is completed, with the administration continuing on a periodic but regular basis over the remaining life span of the mammal. The treatment, which shifts the survival curve, is especially useful for dogs.

4 Claims, 1 Drawing Sheet

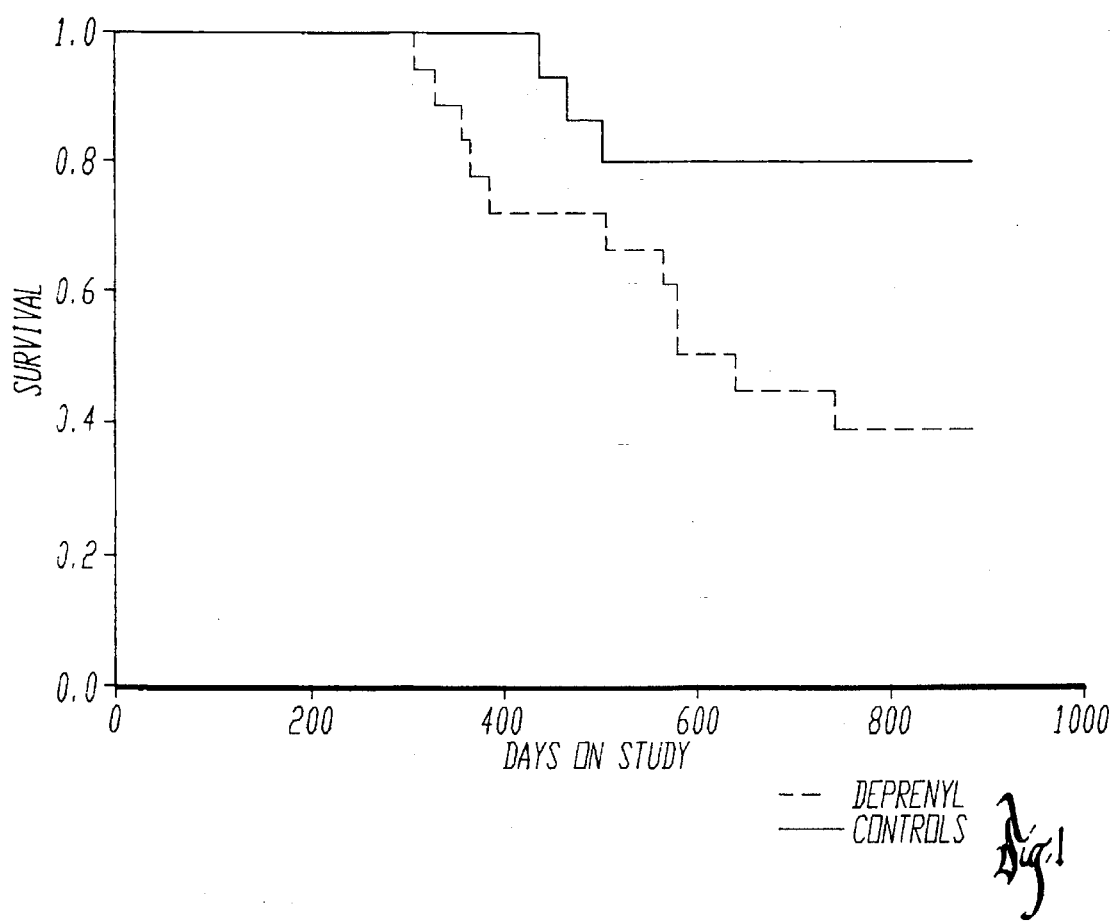

METHOD FOR SURVIVAL CURVE SHIFTING IN DOGS

CROSS-REFERENCE TO A RELATED APPLICATION

This application is a continuation-in-part of Ser. No. 08/113,608 filed Aug. 27, 1993 (now U.S. Pat. No. 5,387,615) which is a continuation of Ser. No. 975,284 filed Nov. 12, 1992, (now U.S. Pat. No. 5,276,057) which is a continuation-in-part of Ser. No. 643,452 filed Jan. 18, 1991 (abandoned), which is a continuation-in-part of Ser. No. 576,011 filed Aug. 31, 1990 (U.S. Pat. No. 5,151,449).

BACKGROUND OF THE INVENTION

"Normal aging" may be an oxymoron. In fact, 'theories' on why mammals "age", meaning experience progressive decline in physiologic function compared with that expected for "young", but "mature" adults of the same species, are numerous. While theories abound, there is no generally recognized theory of aging, nor is there any recognized therapy to "retard the normal aging process".

Caloric restriction may be the most widely accepted means to retard 'normal aging' (Schneider, E., and J. Reed. Modulations of Aging Processes. *Perspectives on Aging and Mortality.* Handbook of the Biology of Aging. 2nd ed. 1985. van Nostrand, Rineholt Co., N.Y. pp.45–76) and (Raloff, J. Searching out how a severe diet slows aging. Science News. Oct. 5, 1991, p. 215). As first described by McCay, he noted that laboratory rats, fed a nutritionally adequate but calorically deficient diet, had longer mean and maximum life expectancies than control rats (McCay, C., Crowell, M., and L. Maynard; The effect of retarded growth upon the length of life span and upon the ultimate body size. J. Nutrition. 10: 1935, pp.63–79). Since chronic caloric restriction also results in retarded growth, and is otherwise impractical, caloric restriction has largely remained a laboratory model.

Other current 'theories of aging' include the 'free radical' or 'oxidative damage' hypothesis (Orr, W., and R. Sohal. Extension of Life-Span by Overexpression of Superoxide Dismutase and Catalase in Drosophila melanogaster. Science. 263: Feb. 25, 1994, pp. 1128–1130) and (Floyd, R. Oxidative Damage to Behavior During Aging. Science. 254: Dec. 13, 1991, p. 1597). Free radicals are small molecules, either oxygen free radicals or hydroperoxides that have an unpaired electron. These chemical species are extremely reactive and cause substantial damage to biomolecules such as proteins, DNA, RNA, and lipids. The resulting accumulative damage is thought to be associated with the declining physiologic functions considered 'aging'. This theory has been directly demonstrated using the life span in mutant fruit flies (Orr, W., and R. Sohal. Extension of Life-Span by Overexpression of Superoxide Dismutase and Catalase in Drosophila melanogaster. Science. 263: Feb. 25, 1994, pp.1128–1130).

Selegiline is a selective monoamine oxidase-B (MAO-B) inhibitor, which is widely used as an adjunct in the treatment of Parkinson's disease. While its most common usage is for the treatment of Parkinson's disease, selegiline was originally developed as an antidepressant agent. Recent testing has indicated that selegiline may have some effect on increasing sexual response in aging animals, and also may have some effect, at least in rats, in increasing the natural life expectancy. However, to date selegiline has only been medically approved by regulatory agencies for use for treatment of Parkinson's disease.

The search for new lines of medication to improve the quality of life in senescence ever continues. This becomes especially important in modern-day society, especially in developed countries, where the proportion of citizens over 65 years of age continues to increase. In sum, the quality of life has become increasingly important in older years, as people continue to experience longer life expectancy.

There is, therefore, a continuing and real need for the development of medications which retard the normal deterioration of certain physiological functions.

It is a primary objective of the present invention to develop a dosage regimen for the use of selegiline to shift the survival curve for a longer lived mammal such as pet dogs, cats or horses. ('Life span' is the inate or inborn maximal biologic life of a species, whereas 'life expectancy' is the predicted actual life or average life of a species. Rarely is the 'life expectancy' as long or equivalent to the biologic 'life span' of a species.) While selegiline is a known compound that has been used to extend the life expectancy of laboratory rodents (Knoll, J., Dallo, J. and T. T. Yen. Striatal Dopamine, Sexual Activity and Lifespan. Longevity of Rats Treated With (—)Deprenyl. Life Sciences. Vol. 45, no. 6. 1989. pp.525–531), (Milgram, N. W., et al. Maintenance on L-Deprenyl Prolongs Life In Aged Male Rats. Life Sciences. Vol. 47, no. 6. 1990. pp.415–420), (Kitani, K., et al. Chronic Treatment of (—)Deprenyl Prolongs The Life Span of Male Fischer 344 Rats. Further Evidence. Life Sciences. Vol. 52, no. 3. 1993. pp.281–288), there is no prior teaching that would allow extrapolation from a short lived species, such as laboratory rats, to the relatively longer lived species such as dogs, cats, horses or even humans.

Like most drugs, selegiline can have diverse physiological effects which are completely dependent upon the dose administered. In accordance with the present invention, selegiline can be used for successful methods of treatment to provide the desired physiological effects enumerated herein, providing that it is used at the dosage levels mentioned herein, and providing it is administered at the periodic intervals and for the time spans mentioned herein. Obviously, when different dosages and levels of treatment are used, the results expressed herein may not be achieved. In fact, at higher doses adverse behavioral effects may be encountered.

SUMMARY OF THE INVENTION

The present invention relates to the process of using a known compound, selegiline, for new uses. In particular, at the dosage levels described herein, providing that the dosage is used for at least the periods of time expressed herein, there is an observed shifting of the survival curve for dogs, providing an extended life expectancy. The treatment is especially useful for domesticated pets, like horses, dogs and cats, as they increase in age, but would be expected to have utility in any longer lived mammalian species, including humans.

BRIEF DESCRIPTION OF THE DRAWINGS

FIG. 1 is a survival curve for the animals involved in Example 1.

DETAILED DESCRIPTION OF THE INVENTION

As earlier stated, the compound that is useful for the method or protocol of the present invention is a known compound, selegiline. Selegiline has the formula (—)-N-α- dimethyl-N-2-propynylbenzene-ethanamine. It can be illustrated by the following graphic formula:

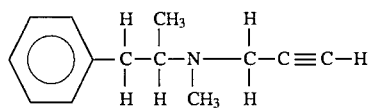

Selegiline also is at times referred to as 1-deprenyl to illustrate that it is a levoratary isomer which is the active form for treatment of Parkinson's disease. Typically, it is provided in a pharmaceutically acceptable salt form thereof, such as the hydrochloride salt.

As used here, pharmaceutically acceptable salt form thereof means the following. Acceptable for use in the pharmaceutical or veterinary art, being nontoxic or otherwise not pharmaceutically or veterinary unacceptable. "Acceptable salt form thereof" means salts formed with inorganic acids such as hydrochloric acid, hydrobromic acid, sulfuric acid, nitric acid, phosphoric acid, and the like, and as well organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, etc.

Administration of the therapeutically active compound selegiline to achieve physiological results of the present invention can be via any of the accepted modes of administration for systemically active substances. These methods include oral, parenteral, and otherwise systemic, aerosol, and topical forms, as well as sustained release systems, etc.

The compositions of the present invention may be any of those known in the pharmaceutical and veterinary arts which are suitable for the method of administration and dosage required in any particular circumstance. In the case of both pharmaceutical and veterinary applications, such compositions may include tablets, pills, capsules, powders, aerosols, suppositories, skin patches, parenterals, and oral liquids including oil/aqueous suspensions, solutions and emulsions. It may include long acting injectables and sustained release devices.

When the dosage is in solid form, solid pharmaceutical carriers such as starch, sugar, talc, mannitol, povidone, magnesium stearate, and the like may be used to form powders. Lactose and mannose are the preferred solid carrier. The powders may be used as such for direct administration to a patient or, instead, the powders may be added to suitable foods and liquids, including water, to facilitate administration.

The powders also may be used to make tablets, or to fill gelatin capsules. Suitable lubricants like magnesium stearate, binders such as gelatin, and disintegrating agents like sodium carbonate, in combination with citric acid, may be used to form the tablets.

Unit dosage forms such as tablets and capsules may contain any suitable predetermined amount of selegiline, advisably as a nontoxic acid addition salt, and may be administered one or more at a time at regular intervals as later described. Such unit dosage form, however, should, with a broad range guideline, contain a concentration of 0.1% to 10% by weight of one or more forms of the active selegiline.

A typical tablet may have the composition:

|   | Mg. |
|---|---|
| 1. Selegiline | 10.0 |
| 2. Mannitol | 100 |
| 3. Stearic acid | 3 |

A granulation is made from the mannitol. The other ingredients are added to the dry granulation and then the tablets are punched.

Another tablet may have the composition:

|   | Mg. |
|---|---|
| 1. Selegiline | 10 |
| 2. Starch U.S.P. | 57 |
| 3. Lactose U.S.P. | 73 |
| 4. Talc U.S.P. | 9 |
| 5. Stearic acid | 6 |

Powders 1, 2 and 3 are slugged, then granulated, mixed with 4 and 5, and tableted.

Capsules may be prepared by filling No. 3 hard gelatin capsules with the following ingredients, thoroughly mixed:

|   | Mg. |
|---|---|
| 1. Selegiline | 5 |
| 2. Lactose U.S.P. | 200 |
| 3. Starch U.S.P. | 16 |
| 4. Talc U.S.P. | 8 |

As earlier expressed, physiological functions effected by the treatment herein with selegiline are necessarily dosage dependent. Put another way, like most drugs, selegiline has diverse physiological effects, depending upon the dose administered. Unless the dose administered is within the levels set forth herein, the desired effects on shifting of the survival curve are not achieved without adverse effects.

While the example later described herein provides data only for dogs, the tests are a fair example for any longer lived mammal, including, without limitation, humans, cattle, horses, swine, dogs, cats, and the like. The treatment may even work for birds or fish.

Humans form quick and strong bonds with their domesticated pets, and these strong bonds increase the desire to keep the animals alive for many years, often well beyond the peak years of the animal species in question. Needless to say, the natural enjoyment of these pets by their owners would be significantly increased as the pets grow older if one could shift their mortality curve in a favorable direction.

The life expectancy of many mammals is now known. For example, while the majority of humans die before age 85, the maximum life span of humans is thought to be between 110 and 120 years. Likewise for dogs, while larger breeds of dogs grow older faster, in 7–10 years, smaller dogs become old between 10 and 13 years. Deeb, B. J., and N. S. Wolf. Studying longevity and morbidity in giant and small breeds of dogs. Veterinary Medicine (Supplement). July, 1994. pp.702–713. Shifting the mortality curve in a favorable direction, such that the pet dog would have an increased life expectancy, would be beneficial for the pet owner and for the pet.

In accordance with the present invention, it has been demonstrated that the dog survival curve can be shifted in a favorable fashion, increasing the dog's life expectancy, if the animal is treated periodically with small, but therapeutically effective, doses of selegiline. The administration must not begin at either a too young age or a too old age. Generally, best results are achieved if administration begins with about 50% of the normal life span completed, and generally within the range of 50% to 75% completed. If treatment begins outside of this range, the benefit may be reduced. This is true whether the treatment begins at a very young age or at an elderly age.

As hereinafter explained, the dosage regimen to achieve these desirable results shows usage at levels from about 0.01 mg/kg of body weight up to about 2.0 mg/kg of body weight from one to seven times weekly, but preferably on alternate days. Most preferably, the dosage level is 0.5 mg/kg of body weight given twice weekly, starting in middle age. Of course, it would be known to those in the art that sustained release systems can be used to provide less frequent dosing to achieve the required dosage level.

It is not known precisely why the use of selegiline at the dosage levels and periodicity expressed herein achieves these results. It is simply not known by what mechanism the compound works, except to say that it is critically important that the dosage be at levels expressed herein.

EXAMPLES

Forty-one pairs of age-matched dogs were maintained under Good Laboratory Practices in an established beagle research colony. The dogs ranged in age from 3.8 years to 16.4 years of age at the commencement of the trial. Half of the dogs were treated with selegiline tablets, given once per day orally, at a dosage of 1 mg/kg of body weight. The other dogs were given placebo tablets daily. The laboratory assistants were "blinded", not knowing which dogs were receiving placebo and which were receiving selegiline. The purpose of the study was to evaluate a variety of physiologic parameters in the animals as they 'aged'.

After approximately 26 months, the study was terminated. In addition to voluminous psysiologic data that was periodically collected on these 82 dogs, a mortality table was prepared and analyzed.

The research laboratory has maintained extensive historical records on the life expectancy of laboratory beagles. They routinely begin to see an accelerated increase in mortality at about 10 years of age, with the median life span of 14 years. Thus, if a shifting of the mortality was to occur, one might expect to see the effect in the animals approximately 10 and 14 years of age. In fact, that is exactly what was encountered.

There was no significant mortality differences in those age-matched pairs that were 15 years of age or older at the start of the trial.

There were no significant mortality differences in those age-matched pairs that were less than 10 years of age at the start of the trial.

However, there was a statistically significant decrease in the mortality of selegiline treated dogs in the 34 age-matched dogs that were between 10 and 15 years of age at the commencement of the trial. Specifically, 11 of 18 (61%) of the controls died during the experimental period, whereas only 4 of the 16 (25%) treated dogs died during the experimental period.

Food consumption was monitored throughout the study, as were body weights. There was no difference in food consumption between the treated and control groups, ruling out caloric restriction as an alternative explanation for the shifting of the survival curve in the selegiline treated group.

FIG. 1 shows the survival curve for the study of this example. The population plotted is the dogs that were approximately 10 years old to 15 years old on the first day of treatment and received treatment for at least 6 months. As illustrated in the curve, one begins to see an increase in survivability in the colony of selegiline treated dogs at about 10 years of age (median life span of 14 years). Selegiline treatment significantly increased (P=0.024) the probability of surviving longer than untreated dogs, as demonstrated by shifting of the survival curve in selegiline treated dogs.

From the above example it can be seen that this invention accomplishes at least all of its stated objectives, particularly for dogs. As will be apparent to those of ordinary skill in the art, certain modifications may be made to the process described for the invention and still achieve the effect of the invention. It is intended that those modifications come within the spirit and scope of the appended claims.

What is claimed is:

1. A method of shifting the survival curve of dogs and thereby increasing their life expectancy, comprising:

administering to the dog, commencing at a point in time when at least 50% of its life span as determined by mortality tables is completed, a small but physiologically effective amount of the compound 1-selegiline, or an acceptable salt form thereof, and continuing the administration on a periodic but regular basis over the remaining life of the dog.

2. The method of claim 1 wherein the life span of the dog is from 50% to 75% completed when administration commences.

3. The method of claim 2 wherein the small but physiologically effective amount of selegiline or acceptable salt form thereof, is from about 0.01 mg/kg of body weight to about 20 mg/kg of body weight.

4. The method of claim 1 wherein the selegiline is the hydrogen chloride addition salt form.

\* \* \* \* \*